United States Patent
Kim et al.

(10) Patent No.: US 10,789,458 B2
(45) Date of Patent: Sep. 29, 2020

(54) HUMAN BEHAVIOR RECOGNITION APPARATUS AND METHOD

(71) Applicant: ELECTRONICS AND TELECOMMUNICATIONS RESEARCH INSTITUTE, Daejeon (KR)

(72) Inventors: Do-Hyung Kim, Daejeon (KR); Jin-Hyeok Jang, Sejong (KR); Jae-Hong Kim, Daejeon (KR); Sung-Woong Shin, Daejeon (KR); Jae-Yeon Lee, Daejeon (KR); Min-Su Jang, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 89 days.

(21) Appl. No.: 16/213,833

(22) Filed: Dec. 7, 2018

(65) Prior Publication Data
US 2020/0074158 A1 Mar. 5, 2020

(30) Foreign Application Priority Data
Aug. 28, 2018 (KR) .......................... 10-2018-0101630

(51) Int. Cl.
*G06K 9/66* (2006.01)
*G06K 9/00* (2006.01)
(Continued)

(52) U.S. Cl.
CPC ........ *G06K 9/00342* (2013.01); *A61B 5/1118* (2013.01); *G06K 9/00275* (2013.01);
(Continued)

(58) Field of Classification Search
CPC .................. G06K 9/00342; G06K 9/00375
(Continued)

(56) References Cited

U.S. PATENT DOCUMENTS 9,886,623 B2  2/2018  Kim
2014/0111418 A1*  4/2014  Lee ....................... G06F 3/0346
345/156
(Continued)

FOREIGN PATENT DOCUMENTS

KR  1020100137963 A  12/2010
KR  10-1023951 B1  3/2011
(Continued)

*Primary Examiner* — Kiet M Doan

(57) ABSTRACT

Disclosed herein are a human behavior recognition apparatus and method. The human behavior recognition apparatus includes a multimodal sensor unit for generating at least one of image information, sound information, location information, and Internet-of-Things (IoT) information of a person using a multimodal sensor, a contextual information extraction unit for extracting contextual information for recognizing actions of the person from the at least one piece of generated information, a human behavior recognition unit for generating behavior recognition information by recognizing the actions of the person using the contextual information and recognizing a final action of the person using the behavior recognition information and behavior intention information, and a behavior intention inference unit for generating the behavior intention information based on context of action occurrence related to each of the actions of the person included in the behavior recognition information.

12 Claims, 6 Drawing Sheets

(51) Int. Cl.
    *A61B 5/11* (2006.01)
    *G06F 3/01* (2006.01)
    *G06N 5/04* (2006.01)
(52) U.S. Cl.
    CPC ........... *G06K 9/00375* (2013.01); *G06K 9/66*
        (2013.01); *A61B 5/1114* (2013.01); *G06F 3/01*
        (2013.01); *G06N 5/047* (2013.01); *G06T*
        *2200/08* (2013.01)
(58) Field of Classification Search
    USPC ...... 725/12, 14, 9; 345/156, 158; 705/14.45;
        726/6
    See application file for complete search history.

(56) References Cited

U.S. PATENT DOCUMENTS

| | | | |
|---|---|---|---|
| 2015/0281775 A1* | 10/2015 | Ramaswamy | H04H 60/45 |
| | | | 725/12 |
| 2017/0053553 A1 | 2/2017 | Jang et al. | |
| 2017/0178011 A1 | 6/2017 | Yeung et al. | |
| 2017/0206454 A1 | 7/2017 | Jihn | |

FOREIGN PATENT DOCUMENTS

| | | |
|---|---|---|
| KR | 10-2016-0000849 A | 1/2016 |
| KR | 10-2018-0048008 A | 5/2018 |

\* cited by examiner

| RECOGNITION TARGET ACTION | ACTION-RELATED CONTEXTUAL INFORMATION ||||||||||
|---|---|---|---|---|---|---|---|---|---|---|
| | INTERACTING OBJECT || HUMAN POSTURE ||| PLACE OF OCCURRENCE |||| ENVIRONMENTAL SOUND | IoT |
| | CONTACT OBJECT | NEARBY OBJECT | STANDING POSTURE | SITTING POSTURE | LYING POSTURE | LIVING ROOM | KITCHEN | MAIN ROOM | BATHROOM | | |
| TAKING FOOD FROM REFRIGERATOR | CONTAINER FOR SIDE DISHES | REFRIGERATOR /TABLE | 0.7 | 0.3 | 0 | 0.1 | 0.9 | 0 | 0 | - | REFRIGERATOR IS OPENED |
| ⋮ | | | | | | | | | | | |
| WASHING FACE | SOAP | WASHSTAND/ TOWEL | 0.9 | 0.1 | 0 | 0 | 0.3 | 0 | 0.7 | WATER SOUND | TAP IS TURNED ON |
| ⋮ | | | | | | | | | | | |
| ⋮ | | | | | | | | | | | |

FIG. 5

| RECOGNITION TARGET ACTION | CONTEXT OF ACTION OCCURRENCE | | SHORT-TERM BEHAVIOR INTENTION | LONG-TERM LIFE PATTERN |
|---|---|---|---|---|
| | IMMEDIATELY PREVIOUS ACTION | IMMEDIATELY SUBSEQUENT ACTION | | |
| TAKING FOOD FROM REFRIGERATOR | CLEANING TABLE | DRINKING WATER | HAVING MEAL | 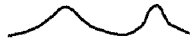 |
| ... | | | | |
| WASHING FACE | BRUSHING TEETH | DRYING OFF WITH TOWEL | GOING OUT |  |
| ... | | | | |
| | | | | |
FIG. 6

HUMAN BEHAVIOR RECOGNITION APPARATUS AND METHOD

CROSS REFERENCE TO RELATED APPLICATION

This application claims the benefit of Korean Patent Application No. 10-2018-0101630, filed Aug. 28, 2018, which is hereby incorporated by reference in its entirety into this application.

BACKGROUND OF THE INVENTION

1. Technical Field

The present invention relates generally to intelligent information technology, and more particularly, to Internet-of-Things (IoT), robot, and human-healthcare technology in which Ubiquitous-Healthcare (U-Healthcare) technology is integrated with intelligent information technology for behavior recognition technology.

2. Description of the Related Art

Due to the rapid advent of an aged society and a rapid increase in the number of elderly persons living alone, it is expected that the quality of lives of elderly persons will deteriorate and that social public spending for supporting the elderly persons will rapidly increase. As one of solutions to this social problem, the development of intelligent information-robot technology is required in order to provide health, life, cognitive or emotional services suitable for a situation by understanding an elderly person and emotionally communicating with the elderly person while a human-care robot lives together with the elderly person.

A human-care robot equipped with such intelligent information technology may provide a personalized care service based on psychological/emotional communion with an elderly person. Also, the elderly-specialized intelligent information technology based on robots may be integrated with existing U-healthcare technology, and may then be actively utilized for medical/healthcare and life-support services.

In order for a robot to provide a human care service to a human being (i.e. a person), the ability to precisely recognize information about the person, which is changing every moment, is basically required, and is referred to as "Who, Where and What (3W) recognition technology". That is, this technology refers to technology including identity recognition technology that recognizes the identity of the person that is the service target, location recognition technology that recognizes where the target person is located, and behavior recognition technology that recognizes what action is being taken by the person.

Among the technologies of the 3W recognition technology, behavior recognition technology for determining what action is being taken by a person is essential technology for understanding/predicting the intention of an action currently taken by an elderly person and detecting the life pattern of the person (the elderly person). A robot may provide a life-support service and a healthcare-support service, which are further improved from an emotional aspect by understanding and sympathizing with a person based on behavior recognition.

Among conventional behavior recognition technologies that are usable in robots, the technology having the highest utilization and reliability is vision-based behavior recognition technology based on the analysis of image data, and the vision-based behavior recognition technology may be classified into three types.

That is, vision-based behavior recognition technology may be classified into video analysis technology for analyzing two-dimensional (2D) images, such as dramas or movies, and detecting an interval during which a specific action occurs in a video, technology for analyzing a depth image that can be acquired from a three-dimensional (3D) camera and a human skeletal structure and recognizing a specific gesture and a unit action, and multimodal behavior recognition technology for merging various types of information acquired from heterogeneous cameras or body-attached sensors in order to improve performance.

All of the conventional behavior recognition technologies temporarily perform one-off recognition using only currently sensed data for taken actions. In other words, the situation and context in which a certain action is initiated are never taken into consideration. Also, the results of recognition are provided and then immediately dissipated without being utilized to improve the performance of a recognition engine.

It is very difficult to expect that the conventional technologies that perform one-off recognition will stably recognize various types of human behavior occurring in a large number of home environments. In particular, changes in various environments and viewpoints due to the movable characteristic of robots make it more and more difficult to perform behavior recognition. In this situation, for highly reliable behavior recognition, there is a need to devise a new method.

Meanwhile, Korean Patent No. 10-1023951 entitled "Motion Recognition System and Method" discloses a system and method that recognizes, in real time, human behavior included in an image captured by a video camera.

SUMMARY OF THE INVENTION

Accordingly, the present invention has been made keeping in mind the above problems occurring in the prior art, and an object of the present invention is to secure the reliability of human behavior recognition in a robot environment, which is very difficult to solve using the above-described conventional technologies.

Another object of the present invention is to provide a new method that can continuously improve the performance of human behavior recognition.

In accordance with an aspect of the present invention to accomplish the above objects, there is provided a human behavior recognition apparatus, including a multimodal sensor unit for generating at least one of image information, sound information, location information, and Internet-of-Things (IoT) information of a person using a multimodal sensor; a contextual information extraction unit for extracting contextual information for recognizing actions of the person from the at least one piece of generated information; a human behavior recognition unit for generating behavior recognition information by recognizing the actions of the person using the contextual information and recognizing a final action of the person using the behavior recognition information and behavior intention information; and a behavior intention inference unit for generating the behavior intention information based on context of action occurrence related to each of the actions of the person included in the behavior recognition information.

The behavior intention inference unit may check actions previous and subsequent to a current action of the person using the behavior recognition information, and then define the context of action occurrence.

The behavior intention inference unit may generate the behavior intention information including possible actions that are capable of occurring subsequent to the actions of the person for whom the context of action occurrence is defined.

The human behavior recognition unit may determine any one of subsequent actions that are predicted from the context of action occurrence included in the behavior intention information, among actions of the person, and then recognize the final action of the person.

The human behavior recognition apparatus may further include a behavior pattern modeling unit for generating a behavior pattern model by modeling a behavior pattern of the person using the contextual information, the behavior recognition information, and the behavior intention information.

The behavior pattern model may include information about a probability of occurrence of each action using times at which the actions of the person are recognized and a frequency with which the contextual information is used to recognize the actions of the person.

The human behavior recognition unit may set weights, corresponding to the action occurrence probability information, for the contextual information for recognizing actions of the person using the behavior pattern model.

The human behavior recognition unit may recognize the final action of the person, among possible actions of the person that are capable of occurring in a current time span, using the contextual information for which the weights are set and the action occurrence probability information.

The behavior pattern modeling unit may update the action occurrence probability information based on times at which the actions of the person are recognized using the behavior pattern model, the contextual information corresponding to the actions of the person, and the behavior intention information.

In accordance with another aspect of the present invention to accomplish the above objects, there is provided a human behavior recognition method for a human behavior recognition apparatus, including generating at least one of image information, sound information, location information, and Internet-of-Things (IoT) information of a person using a multimodal sensor; extracting contextual information for recognizing actions of the person from the at least one piece of generated information; generating behavior recognition information by recognizing the actions of the person using the contextual information; generating the behavior intention information based on context of action occurrence related to each of the actions of the person included in the behavior recognition information; and recognizing a final action of the person using the behavior recognition information and behavior intention information.

Generating the behavior intention information may be configured to check actions previous and subsequent to a current action of the person using the behavior recognition information and then to define the context of action occurrence.

Generating the behavior intention information may be configured to generate the behavior intention information including possible actions that are capable of occurring subsequent to the actions of the person for whom the context of action occurrence is defined.

Recognizing the final action of the person may be configured to determine any one of subsequent actions that are predicted from the context of action occurrence included in the behavior intention information, among actions of the person, and then recognize the final action of the person.

The human behavior recognition method may further include generating a behavior pattern model by modeling a behavior pattern of the person using the contextual information, the behavior recognition information, and the behavior intention information.

The behavior pattern model may include information about a probability of occurrence of each action using times at which the actions of the person are recognized and a frequency with which the contextual information is used to recognize the actions of the person.

Recognizing the final action of the person may be configured to set weights, corresponding to the action occurrence probability information, for the contextual information for recognizing actions of the person using the behavior pattern model.

Recognizing the final action of the person may be configured to recognize the final action of the person, among possible actions of the person that are capable of occurring in a current time span, using the contextual information for which the weights are set and the action occurrence probability information.

Generating the behavior pattern model may be configured to update the action occurrence probability information based on times at which the actions of the person are recognized using the behavior pattern model, the contextual information corresponding to the actions of the person, and the behavior intention information.

BRIEF DESCRIPTION OF THE DRAWINGS

The above and other objects, features and advantages of the present invention will be more clearly understood from the following detailed description taken in conjunction with the accompanying drawings, in which:

FIGS. 5 and 6 are diagrams illustrating a human behavior pattern model according to an embodiment of the present invention.

DESCRIPTION OF THE PREFERRED EMBODIMENTS

Figure 1:
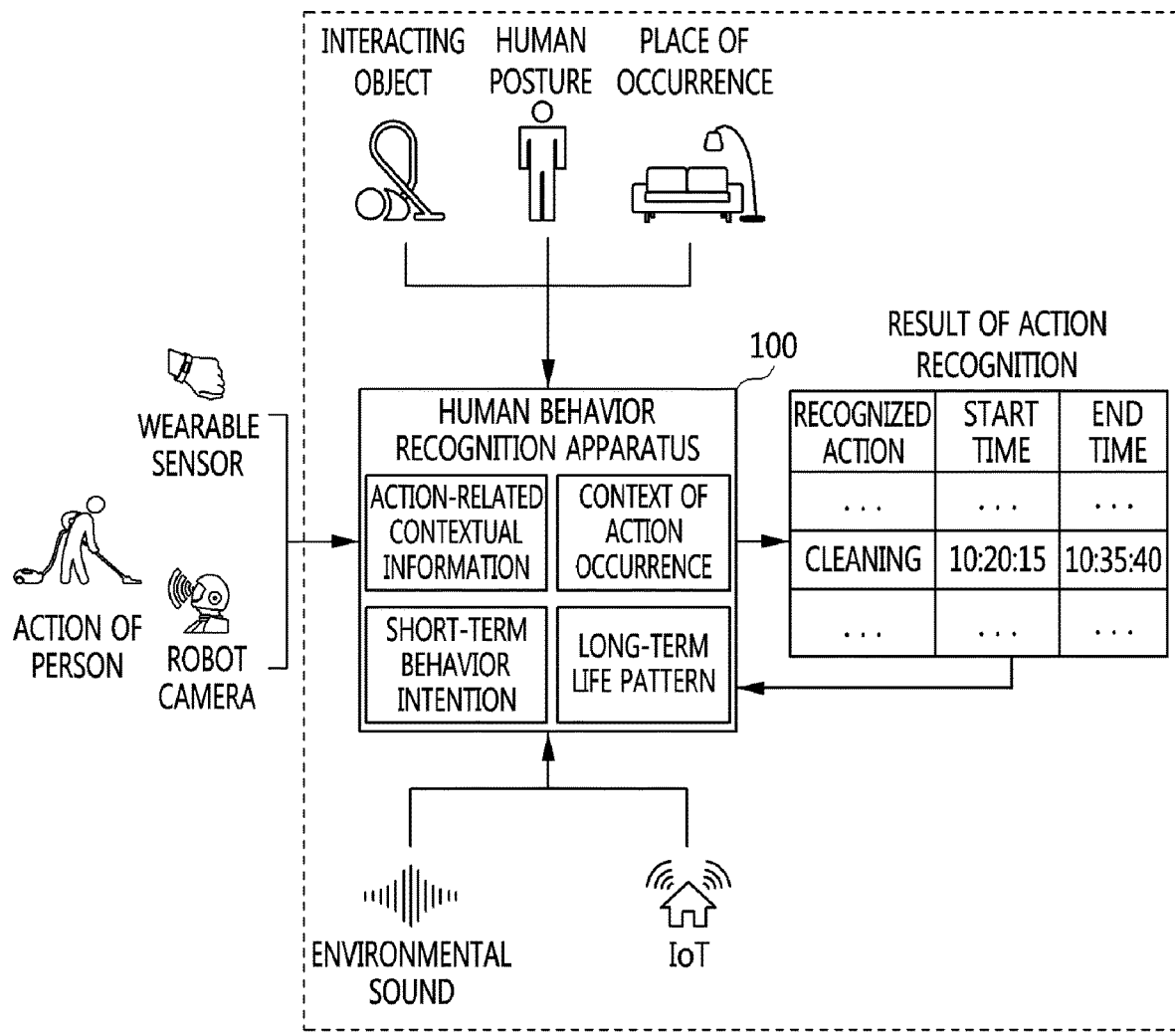
FIG. 1 is a diagram illustrating a human behavior recognition system according to an embodiment of the present invention.

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

In the present specification, it should be understood that terms such as "include" or "have" are merely intended to indicate that features, numbers, steps, operations, components, parts, or combinations thereof are present, and are not intended to exclude a possibility that one or more other features, numbers, steps, operations, components, parts, or combinations thereof will be present or added.

Hereinafter, preferred embodiments of the present invention will be described in detail with reference to the attached drawings.

FIG. 1 is a diagram illustrating a human behavior recognition system according to an embodiment of the present invention.

Referring to FIG. 1, in the human behavior recognition system according to the embodiment of the present invention, a human behavior recognition apparatus 100 may capture an image of the action of a human being (i.e. a person), receive data generated by a wearable sensor worn by the person, and recognize the action of the person.

The human behavior recognition apparatus 100 may be a computing device that includes a camera, a microphone, a data transmission/reception module, etc. corresponding to a multimodal sensor and that recognizes human behavior (i.e. each action of a person), and may be a human behavior recognition robot that is mounted therein to recognize human behavior and that interacts with each person.

Here, the human behavior recognition apparatus 100 may recognize the posture of the person and an object interacting with the person from the image information of the person captured using the camera, and may also recognize environmental sounds or conversation sounds in the place where the person is located from sound information generated using the microphone.

Here, the human behavior recognition apparatus 100 may recognize the place where the corresponding action occurs from the location information of the place where the person is located by utilizing a wearable sensor worn by the person or the absolute coordinates of indoor map data.

The human behavior recognition apparatus 100 may recognize the action of the person using IoT information provided by IoT equipment in an indoor area in which the person is located.

That is, the human behavior recognition apparatus 100 may generate at least one of image information, sound information, location information, and IoT information related to the person using the multimodal sensor, and may then extract action-related contextual information.

Here, the human behavior recognition apparatus 100 may generate behavior recognition information by recognizing individual actions of the person from the action-related contextual information, and may define the context of action occurrence from the generated behavior recognition information.

The human behavior recognition apparatus 100 may infer a short-term behavior intention depending on the context of action occurrence, may recognize actions of the person in respective time spans, and may generate a long-term life pattern of the person from the context of action occurrence and the short-term behavior intention.

The human behavior recognition apparatus 100 may recognize the actions of the person, may continuously update information about the long-term life pattern in relation to the action-related contextual information, the context of action occurrence, and the short-term behavior intention, and may more accurately and reliably recognize the actions of the person using the information about the long-term life pattern.

Here, the human behavior recognition apparatus 100 may output information about the ultimately recognized action of the person, the start time of the action, and the end time of the action as the results of the ultimately recognized action of the person.

Figure 2:
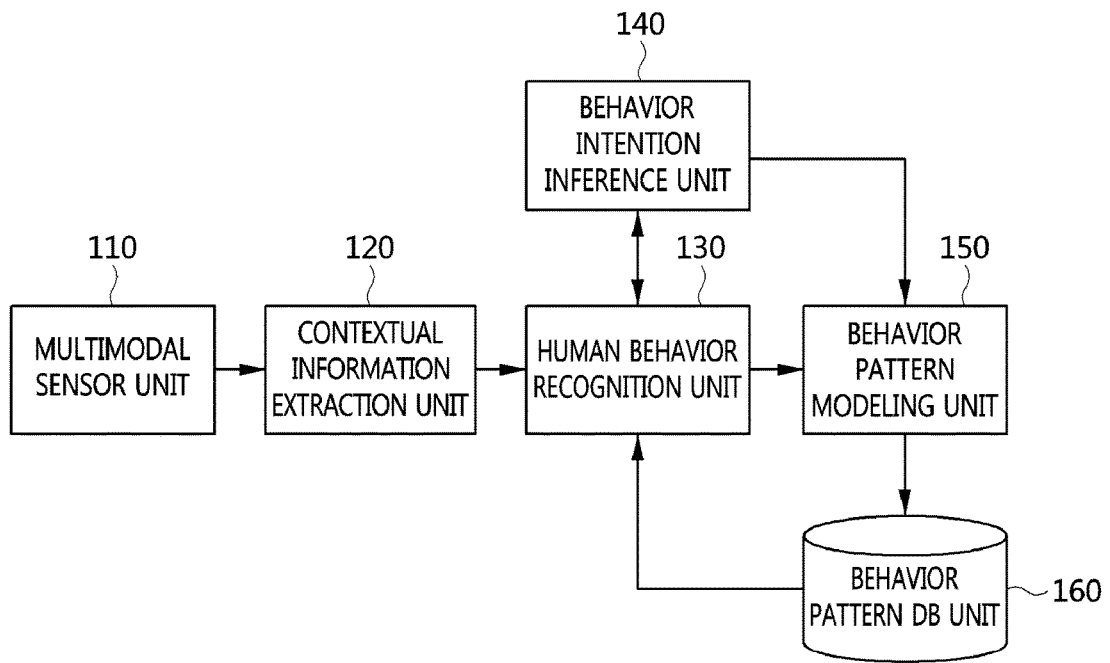
FIG. 2 is a block diagram illustrating a human behavior recognition apparatus according to an embodiment of the present invention.
Figure 3:
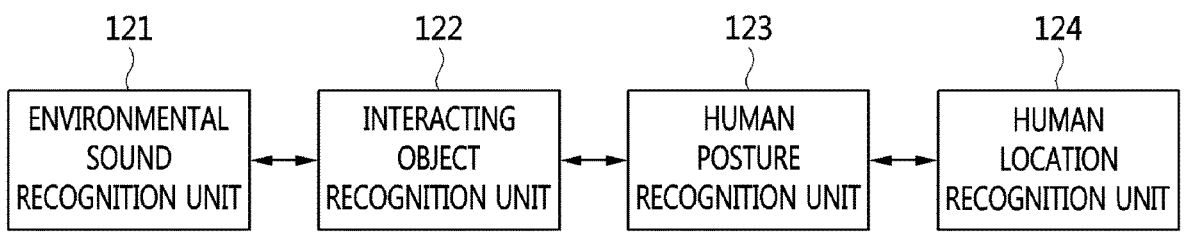
FIG. 3 is a block diagram illustrating in detail an example of the contextual information extraction unit of FIG. 2.

FIG. 2 is a block diagram illustrating a human behavior recognition apparatus according to an embodiment of the present invention. FIG. 3 is a block diagram illustrating in detail an example of the contextual information extraction unit of FIG. 2.

Referring to FIG. 2, the human behavior recognition apparatus 100 according to an embodiment of the present invention includes a multimodal sensor unit 110, a contextual information extraction unit 120, a human behavior recognition unit 130, a behavior intention inference unit 140, a behavior pattern modeling unit 150, and a behavior pattern database (DB) unit 160.

The multimodal sensor unit 110 may include a camera, a microphone, a position sensor, and a data transmission/reception module.

The multimodal sensor unit 110 may generate image information obtained by capturing an image of a person using the camera.

The multimodal sensor unit 110 may generate sound information by recording sounds generated at the place where the person is located using the microphone.

The multimodal sensor unit 110 may generate location information from coordinate information indicated in data of an indoor map of the place where the person is located using the position sensor.

Here, the multimodal sensor unit 110 may also receive the location information of the person from the wearable sensor worn by the person.

The multimodal sensor unit 110 may receive state information provided by IoT equipment interacting with the person and then generate IoT information.

The contextual information extraction unit 120 may extract contextual information for recognizing the action of the person from at least one of the image information, sound information, location information, and IoT information of the person, which are generated using the multimodal sensor.

Referring to FIG. 3, the contextual information extraction unit 120 may include an environmental sound recognition unit 121, an interacting object recognition unit 122, a human posture recognition unit 123, and a human location recognition unit 124.

The environmental sound recognition unit 121 may recognize and extract environmental sounds and human conversation sounds from sound information.

Here, the environmental sound recognition unit 121 may determine the types of sounds based on the recognized environmental sounds and conversation sounds, and may extract the determined sound types as contextual information.

For example, the environmental sound recognition unit 121 may identify a doorbell-ringing sound, a door-opening sound, or a telephone-ringing sound from the recognized environmental sounds.

By means of identification of these sounds, the human behavior recognition apparatus 100 may recognize the current possible action of the person based on the contextual information about the environmental sounds extracted from the sound information.

The interacting object recognition unit 122 may recognize the person from the image information, and may recognize and extract an object that is in contact with the person or that is close to the person.

Here, the interacting object recognition unit 122 may determine the type of the recognized object, and may extract the determined object type as contextual information.

For example, the interacting object recognition unit 122 may recognize whether the object held in the person's hand is a screwdriver, a key, a phone or the like.

By this recognition, the human behavior recognition apparatus 100 may recognize the current possible action of the person based on the contextual information of the person that is extracted from the image information.

Also, the interacting object recognition unit 122 may receive IoT information from IoT equipment that interacts with the person, and may then extract contextual information related to the current action.

For example, when an object interacting with the person is a refrigerator and the refrigerator is IoT equipment, the interacting object recognition unit 122 may receive IoT information related to the opening of the door of the refrigerator when the door of the refrigerator is opened.

The human posture recognition unit 123 may recognize the person from the image information, and may recognize and extract the posture of the person.

The human posture recognition unit 123 may determine the recognized posture of the person and extract the determined posture as contextual information.

For example, the human posture recognition unit 123 may determine the recognized posture of the person to be 'standing', 'sitting on a chair', 'lying on the ground', 'lying on his or her face', or the like.

By means of this, the human behavior recognition apparatus 100 may recognize the current possible action of the person based on the contextual information related to the posture of the person extracted from the image information.

The human location recognition unit 124 may recognize the place where the person is located from location information, and may extract coordinate information related to the location or the place of action occurrence as contextual information.

For example, the human location recognition unit 124 may provide the location information in the form of absolute coordinates such as (x, y, z), or in the form of information such as a living room, a kitchen, or the entrance defined as the place where the person is located.

By means of this, the human behavior recognition apparatus 100 may recognize the current possible action of the person based on the contextual information related to the place of action occurrence, extracted from the location information.

That is, the human behavior recognition apparatus 100 may extract the current contextual information of the person under various conditions, and may reduce the number of cases of human behavior that may occur through the extracted contextual information, thus improving the recognition performance of human behavior.

The human behavior recognition unit 130 may generate behavior recognition information by recognizing individual actions of the person using the contextual information, and may recognize the final action of the person using the behavior recognition information and behavior intention information.

The human behavior may be classified depending on the major classification, middle classification, and minor classification, and detailed actions thereof may be defined as shown in the following Tables 1 and 2.

TABLE 1

| Major classification | Middle classification | Minor classification | Detailed actions |
|---|---|---|---|
| Normal action | Simple action | State | Stand |
|  |  |  | Sit |
|  |  |  | Lie down |
|  |  |  | Raise hand |
|  |  | Action | Walk |
|  |  |  | Run |
|  | Normal indoor action | Daily action | Wash face |
|  |  |  | Brush teeth |
|  |  |  | Eat rice with a spoon |
|  |  |  | Eat fruit with a fork |
|  |  |  | Drink water |
|  |  |  | Put on/take off clothes |
|  |  |  | Put on makeup |
|  |  |  | Comb hair |
|  |  |  | Make a call |
|  |  |  | View a smartphone |
|  |  |  | Write characters |
|  |  |  | Smoke |
|  |  |  | Clap hands |
|  |  |  | Pour drink |
|  |  | Housekeeping activity | Chop food |
|  |  |  | Wash dishes |
|  |  |  | Vacuum |
|  |  |  | Wipe the floor |
|  |  | Leisure activity | Play the piano |
|  |  |  | Play the violin |
|  |  |  | Play the guitar |
|  |  |  | Dance |
|  |  |  | Read a book |
|  |  |  | Read a newspaper |
|  |  |  | Watch TV |
|  |  |  | Sew |
|  |  |  | Use computer |

TABLE 2

| Major classification | Middle classification | Minor classification | Detailed actions |
|---|---|---|---|
| Human-care robot-specific action | Elderly person-specific action | Health-promoting activity | Take medicine |
|  |  |  | Do free exercise |
|  |  | Special action | Travel with a wheelchair |
|  |  |  | Crawl |
|  |  |  | Fall down |
|  | Human-Human (HH) interaction |  | Have a conversation |
|  |  |  | Shake hands |
|  |  |  | Embrace each other |
|  |  |  | Fight |
|  | Human-Robot (HR) interaction |  | Beckon with the hand |
|  |  |  | Greet from side to side |
|  |  |  | Laugh brightly |

Here, when the human behavior recognition apparatus 100 is initially driven, contextual information and behavior intention information related to the action of the person may not be present. Accordingly, the human behavior recognition unit 130 may receive initial weight information, which corresponds to the contextual information and behavior intention information and is arbitrarily assigned by a developer based on common sense, or may directly receive weight information by directly asking questions to specific persons. However, as the human behavior recognition apparatus 100 starts to calculate the results of behavior recognition, such information may be continuously updated, and information customized for a specific person may be gradually generated from normal information.

The behavior intention inference unit 140 may generate behavior intention information based on context of action occurrence related to each of the actions of the person included in the behavior recognition information.

Here, the behavior intention inference unit 140 may define the context of action occurrence by checking actions previous and subsequent to the current action of the person using the behavior recognition information.

Here, the behavior intention inference unit 140 may generate behavior intention information that includes possible actions that may occur subsequent to the actions of the person for whom the context of action occurrence has been defined.

The behavior intention information may correspond to contextual information related to the sequence of occurrence of individual actions. The behavior intention information may be implemented as a set of certain daily actions, and may be obtained by defining the regularity of the sequence of occurrence of element actions, included in the set, as the context of action occurrence, thus improving the accuracy and reliability of human behavior recognition.

For example, in the behavior intention information, when the current action is "pouring water into a cup", the subsequent action may be predicted as "drinking water", "taking medicine", or the like. When the currently recognized action is "brushing teeth", the probability that actions related to washing-up, such as "washing face", "washing hair" or "drying off with a towel" will occur may be increased, and thus these actions may be included in the behavior intention information.

Further, the behavior intention inference unit 140 may infer a short-term behavior intention for a series of sequences composed of the previous action, the current action, and the subsequent action, and may then generate behavior intention information from the short-term behavior intention.

For example, when the previous action is recognized as "brushing teeth", the current action is recognized as "washing face", and the subsequent action is recognized as "drying off with a towel", the behavior intention inference unit 140 may infer the short-term behavior intention as 'going out', and then generate the behavior intention information.

Here, the human behavior recognition unit 130 may determine any one of subsequent actions predicted from the context of action occurrence included in the behavior intention information, among the actions of the person, and may then recognize the final action of the person.

The human behavior recognition unit 130 may set the weights of actions included in the behavior intention information to high values, may determine any one of subsequent actions, the weights of which are set to high values, from the currently recognized action using the context of action occurrence, and may then recognize the final action of the person.

The behavior pattern modeling unit 150 may generate a behavior pattern model by modeling the human behavior pattern of the person using the contextual information, the behavior recognition information, and the behavior intention information.

The behavior pattern DB unit 160 may store the behavior pattern model generated by the behavior pattern modeling unit 150.

Here, the behavior pattern model may include action occurrence probability information using the times at which the actions of the person are recognized and the frequency with which the contextual information is used to recognize the actions of the person.

When the human behavior recognition apparatus 100 is initially driven, a behavior pattern model for the person may not be present, and thus the behavior pattern modeling unit 150 may mainly perform recognition using the contextual information and the behavior intention information. However, when the contextual information and the behavior intention information related to the results of behavior recognition are accumulated as time elapses, the behavior pattern modeling unit 150 may generate a behavior pattern model by modeling the behavior pattern of a specific person.

The human behavior recognition unit 130 may set weights corresponding to the action occurrence probability information for the contextual information for recognizing the actions of the person using the behavior pattern model.

Here, the human behavior recognition unit 130 may recognize the final action of the person, among the actions of the person that may occur in the current time span, based on the contextual information, for which the weights are set, and the action occurrence probability information.

The behavior pattern modeling unit 150 may update the action occurrence probability information based on the times at which the actions of the person are recognized using the behavior pattern model, the contextual information corresponding to the actions of the person, and the behavior intention information.

Further, the human behavior recognition unit 130 may multiply an observed value for the final action of the person that is recognized using both the contextual information for recognizing the actions of the person and the behavior intention information by the weight of the behavior pattern model, and may then calculate a weighted sum thereof as a final action recognition score.

As described above, in the human behavior recognition apparatus 100 according to the embodiment of the present invention, various methods other than the above-described method may also be applied as the method for complementarily combining the contextual information for recognizing the actions of each person, the behavior intention information, and the behavior pattern model.

Figure 4:
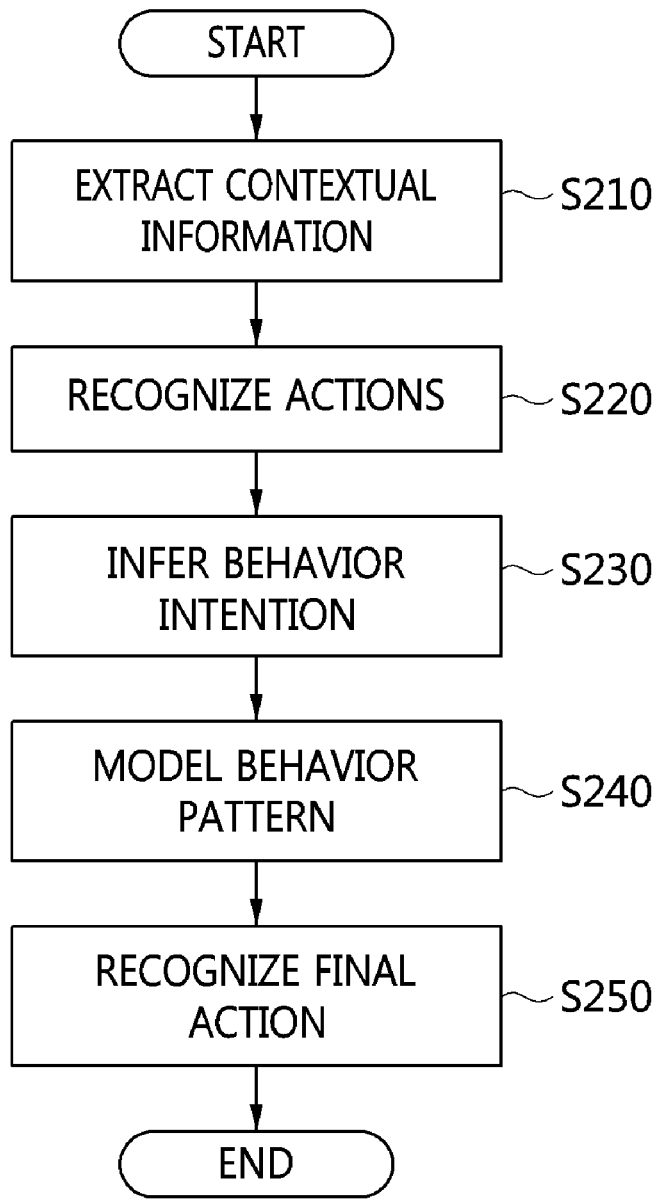
FIG. 4 is an operation flowchart illustrating a human behavior recognition method according to an embodiment of the present invention.

FIG. 4 is an operation flowchart illustrating a human behavior recognition method according to an embodiment of the present invention.

Referring to FIG. 4, in the human behavior recognition method according to the embodiment of the present invention, contextual information may be extracted at step S210.

That is, at step S210, at least one of image information, sound information, location information, and IoT information of the person may be generated using a multimodal sensor, and contextual information for recognizing the actions of the person may be extracted from the at least one piece of information.

At step S210, image information obtained by capturing an image of a person using the camera may be generated.

At step S210, sound information may be generated by recording sounds generated at the place where the person is located using the microphone.

At step S210, location information may be generated from coordinate information indicated in data of an indoor map of the place where the person is located using the position sensor.

At step S210, the location information of the person may also be received from the wearable sensor worn by the person.

At step S210, state information provided by IoT equipment interacting with the person may be received and then IoT information may be generated.

At step S210, contextual information for recognizing the action of the person may be extracted from at least one of the image information, sound information, location information, and IoT information of the person, which are generated using the multimodal sensor.

Here, at step S210, environmental sounds and human conversation sounds may be recognized and extracted from sound information.

At step S210, the types of sounds may be determined based on the recognized environmental sounds and conversation sounds, and the determined sound types may be extracted as contextual information.

For example, at step S210, a doorbell-ringing sound, a door-opening sound, or a telephone-ringing sound may be identified from the recognized environmental sounds.

At step S210, the person may be recognized from the image information, and an object that is in contact with the person or that is close to the person may be recognized and extracted.

At step S210, the type of the recognized object may be determined, and the determined object type may be extracted as contextual information.

For example, at step S210, whether the object held in the person's hand is a screwdriver, a key, a phone or the like may be recognized.

Further, at step S210, IoT information may be received from IoT equipment that interacts with the person, and then contextual information related to the current action may be extracted.

For example, at step S210, when an object interacting with the person is a refrigerator and the refrigerator is IoT equipment, IoT information related to the opening of the door of the refrigerator may be received when the door of the refrigerator is opened.

At step S210, the person may be recognized from the image information, and the posture of the person may be recognized and extracted.

Here, at step S210, the recognized posture of the person may be determined and extracted as contextual information.

At step S210, the recognized posture of the person may be determined to be 'standing', 'sitting on a chair', 'lying on the ground', 'lying on his or her face', or the like.

At step S210, the place where the person is located may be recognized from location information, and coordinate information related to the location or the place of action occurrence may be extracted as contextual information.

For example, at step S210, the location information may be provided in the form of absolute coordinates such as (x, y, z), or in the form of information such as a living room, a kitchen, or the entrance defined as the place where the person is located.

Further, in the human behavior recognition method according to the embodiment of the present invention, the actions of the person may be recognized at step S220.

That is, at step S220, behavior recognition information may be generated by recognizing the individual actions of the person using the contextual information.

Next, in the human behavior recognition method according to the embodiment of the present invention, the behavior intention of the person may be inferred at step S230.

That is, at step S230, behavior intention information may be generated based on context of action occurrence related to each of the actions of the person included in the behavior recognition information.

At step S230, the context of action occurrence may be defined by checking actions previous and subsequent to the current action of the person using the behavior recognition information.

In this case, at step S230, behavior intention information, including possible actions that may occur subsequent to the actions of the person for whom the context of action occurrence has been defined, may be generated.

The behavior intention information may correspond to contextual information related to the sequence of occurrence of individual actions. The behavior intention information may be implemented as a set of certain daily actions, and may be obtained by defining the regularity of the sequence of occurrence of element actions, included in the set, as the context of action occurrence, thus improving the accuracy and reliability of human behavior recognition.

For example, in the behavior intention information, when the current action is "pouring water into a cup", the subsequent action may be predicted as "drinking water", "taking medicine", or the like. When the currently recognized action is "brushing teeth", the probability that actions related to washing-up, such as "washing face", "washing hair" or "drying off with a towel" will occur may be increased, and thus these actions may be included in the behavior intention information.

Further, at step S230, a short-term behavior intention for a series of sequences composed of the previous action, the current action, and the subsequent action may be inferred, and then behavior intention information may be generated from the short-term behavior intention.

For example, at step S230, when the previous action is recognized as "brushing teeth", the current action is recognized as "washing face", and the subsequent action is recognized as "drying off with a towel", the short-term behavior intention may be inferred as 'going out', and then the behavior intention information may be generated.

Next, in the human behavior recognition method according to the embodiment of the present invention, a behavior pattern may be modeled at step S240.

That is, at step S240, a behavior pattern model may be generated by modeling the human behavior pattern of the person using the contextual information, the behavior recognition information, and the behavior intention information.

At step S240, the generated behavior pattern model generated by the behavior pattern modeling unit 150 may be stored.

Here, the behavior pattern model may include action occurrence probability information using the times at which the actions of the person are recognized and the frequency with which the contextual information is used to recognize the actions of the person.

Next, in the human behavior recognition method according to the embodiment of the present invention, the final action of the person may be recognized at step S250.

That is, at step S250, the final action of the person may be recognized using both the behavior recognition information and the behavior intention information.

At step S250, any one of subsequent actions predicted from the context of action occurrence included in the behavior intention information may be determined, among the actions of the person, and then the final action of the person may be recognized.

At step S250, the weights of actions included in the behavior intention information may be set to high values, any one of subsequent actions, the weights of which are set to high values, may be determined from the currently recognized action using the context of action occurrence, and then the final action of the person may be recognized.

At step S250, weights corresponding to the action occurrence probability information may be set for the contextual information for recognizing the actions of the person using the behavior pattern model.

Here, at step S250, the final action of the person, among the actions of the person that may occur in the current time span, may be recognized based on the contextual information, for which the weights are set, and the action occurrence probability information.

At step S250, the action occurrence probability information may be updated based on the times at which the actions of the person are recognized using the behavior pattern model, the contextual information corresponding to the actions of the person, and the behavior intention information.

Further, at step S250, an observed value for the final action of the person that is recognized using both the contextual information for recognizing the actions of the person and the behavior intention information may be multiplied by the weight of the behavior pattern model, and then a weighted sum thereof may be calculated as a final action recognition score.

As described above, in the human behavior recognition method for the human behavior recognition apparatus 100 according to the embodiment of the present invention, various methods other than the above-described method may also be applied as the method for complementarily combining the contextual information for recognizing the actions of each person, the behavior intention information, and the behavior pattern model.

FIGS. 5 and 6 are diagrams illustrating a human behavior pattern model according to an embodiment of the present invention.

Referring to FIG. 5, action-related contextual information in the human behavior pattern model according to the embodiment of the present invention may include an interacting object, a human posture, a place of occurrence, an environmental sound, and IoT information in relation to each recognition target action.

Here, the interacting object may include information about a contact object and nearby objects.

The contact object may include information about an object which is touched by the person or which is held in the hand of the person.

For example, it can be seen that, for the action of the person, that is, 'taking food from the refrigerator', the contact object touched by the person is a 'container for side dishes', and the nearby objects are 'refrigerator/table'.

The human posture may include a standing posture, a sitting posture, and a lying posture, and may further include other postures.

Here, the human posture may include the probability that the recognition target action will occur for each of the postures, or the rate of the occurrence of the recognition target action.

For example, it can be seen that the occurrence rate of the action of the person 'taking food from refrigerator' for each human posture is '0.7' for a standing posture, '0.3' for a sitting posture, and '0' for a lying posture.

Therefore, when the human behavior recognition apparatus 100 recognizes the human posture of the person as a 'standing posture' from extracted contextual information, a high weight or a high probability of occurrence may be assigned to the action 'taking food from the refrigerator', whereas when the human behavior recognition apparatus 100 recognizes the human posture as a 'lying posture', the action 'taking food from the refrigerator' may be excluded such that it is not recognized.

Also, the place of occurrence may include places such as a living room, a kitchen, a main room, and a bathroom, and may further include other places.

Here, the place of occurrence may include the probability that the recognition target action will occur at each of the places, or the occurrence rate of the recognition target action.

For example, it can be seen that, for the action of the person 'taking food from the refrigerator', the occurrence rate of the action in the living room is '0.1', the occurrence rate of the action in the kitchen is '0.9', and the occurrence rate of the action in the main room and the bathroom is '0'.

Therefore, when the human behavior recognition apparatus 100 recognizes the place of occurrence of the action as a 'kitchen' from the extracted contextual information, a high weight or a high probability of occurrence may be assigned to the action 'taking food from the refrigerator', whereas when the human behavior recognition apparatus 100 recognizes the place of occurrence of the action as a 'main room' or a 'bathroom', the action 'taking food from the refrigerator' may be excluded such that it is not recognized.

Further, the environmental sound may include information about environmental sounds extracted from the contextual information.

For example, it can be seen that, for the action of the person 'washing face', the environmental sound having the highest association with the action is 'water sound'. When the human behavior recognition apparatus 100 recognizes the environmental sound as 'water sound' from the extracted contextual information, a high weight or a high probability of occurrence may be assigned to the action 'washing face'.

Further, the IoT information may include state information which is extracted from the contextual information and provided by IoT equipment.

For example, it can be seen that, for the action of the person 'taking food from the refrigerator', the IoT information may be 'refrigerator is opened'. When the IoT equipment is a refrigerator and the human behavior recognition apparatus 100 recognizes IoT information related to 'refrigerator is opened' from the contextual information extracted using the IoT equipment, a high weight or high probability of occurrence may be assigned to the action 'taking food from the refrigerator'.

Referring to FIG. 6, it can be seen that the human behavior pattern model according to an embodiment of the present invention includes information about the context of action occurrence, a short-term behavior intention, and a long-term life pattern in relation to behavior intention information.

The context of action occurrence may include information about an action immediately previous to and an action immediately subsequent to a recognition target action.

For example, it can be seen that, for the action of a person 'taking food from the refrigerator', the immediately previous action included in the context of action occurrence is 'cleaning the table', and the immediately subsequent action is 'drinking water'.

Therefore, when the action recognized by the human behavior recognition apparatus 100 is 'cleaning the table', a high weight or a high probability of occurrence may be assigned to the action 'taking food from the refrigerator' as the subsequent action to be recognized. Further, when the action recognized by the human behavior recognition apparatus 100 is 'taking food from the refrigerator', a high weight or a high probability of occurrence may be assigned to the action 'drinking water' as the subsequent action to be recognized.

Also, the short-term behavior intention may include information about the behavior intention of the person related to the recognition target action inferred from the context of action occurrence.

For example, when a series of actions that are recognized is 'cleaning the table', 'taking food from the refrigerator', and 'drinking water', the human behavior recognition apparatus 100 may recognize the actions as short-term behavior intentions related to 'having a meal', and a high weight or a high probability of occurrence may be assigned to actions related to 'having a meal'.

Also, the long-term life pattern may include information about the probability distribution of a recognition target action in a specific time span by accumulating information about the actions of the person recognized in respective time spans.

For example, for the action of the person 'taking food from the refrigerator', when a short-term behavior intention is recognized as 'having a meal', a high weight or a high probability of occurrence may be assigned to the corresponding time span with reference to the long-term life pattern in which actions related to 'having a meal' occur.

Therefore, when the current time is 12 p.m., it corresponds to a lunch time, and thus the human behavior recognition apparatus 100 may assign a higher weight or a high probability of occurrence to actions related to the short-term behavior intention, that is, 'having a meal' depending on the long-term life pattern.

By means of this, the human behavior recognition apparatus 100 may more accurately recognize the actions of the person using the behavior pattern model.

Furthermore, the human behavior recognition apparatus 100 may update the behavior pattern model based on contextual information, behavior intention information, and various types of information which are used to recognize the actions of the person, thus continuously improving human behavior recognition performance.

Figure 7:
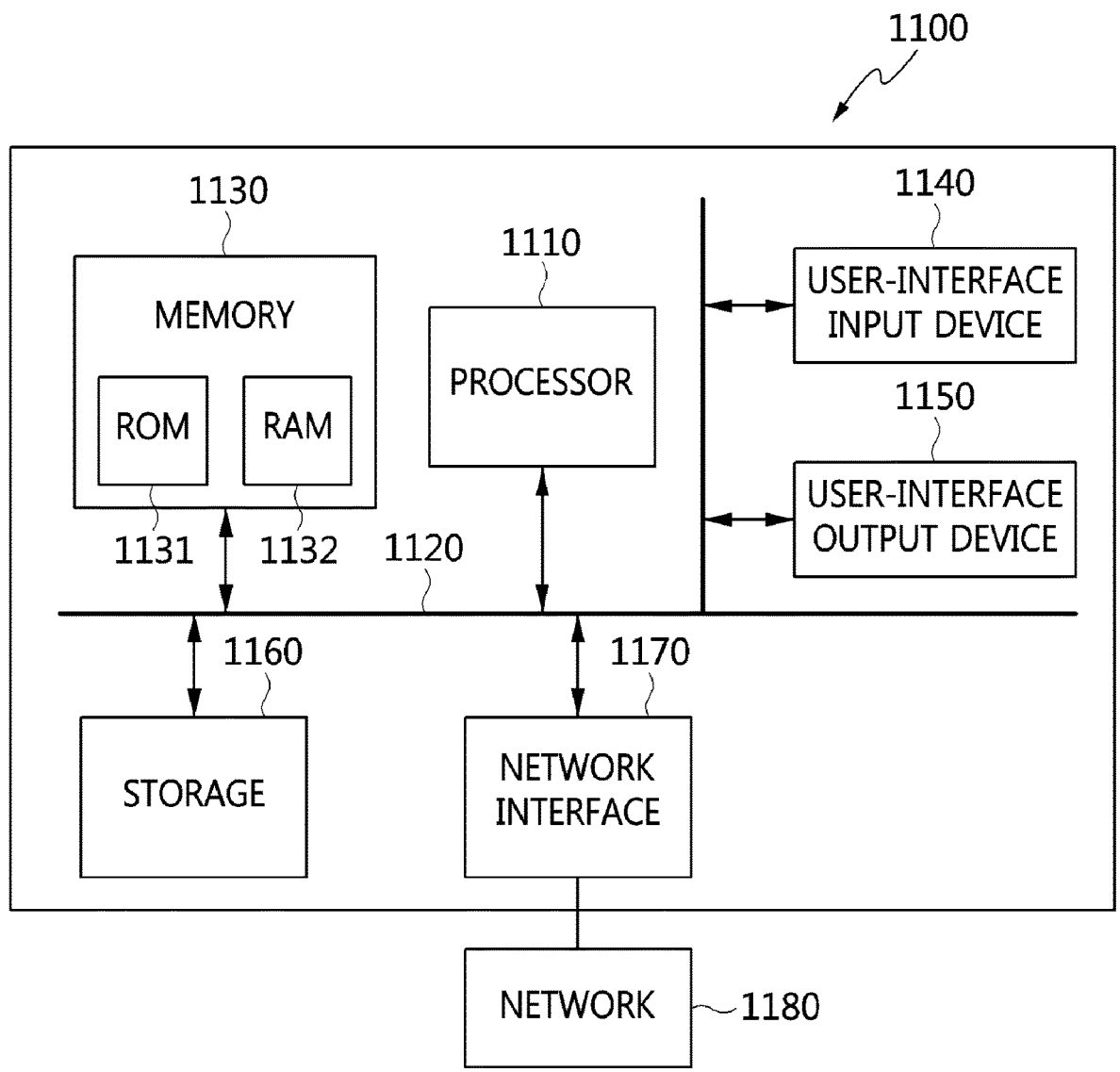
FIG. 7 is a diagram illustrating a computer system according to an embodiment of the present invention.

FIG. 7 is a diagram illustrating a computer system according to an embodiment of the present invention.

Referring to FIG. 7, the human behavior recognition apparatus 100 according to an embodiment of the present invention may be implemented in a computer system 1100 such as a computer-readable storage medium. As illustrated in FIG. 7, the computer system 1100 may include one or more processors 1110, memory 1130, a user interface input device 1140, a user interface output device 1150, and storage 1160, which communicate with each other through a bus 1120. The computer system 1100 may further include a network interface 1170 connected to a network 1180. Each processor 1110 may be a Central Processing Unit (CPU) or a semiconductor device for executing processing instructions stored in the memory 1130 or the storage 1160. Each of the memory 1130 and the storage 1160 may be any of various types of volatile or nonvolatile storage media. For example, the memory 1130 may include Read-Only Memory (ROM) 1131 or Random Access Memory (RAM) 1132.

The present invention may secure the reliability of human behavior recognition in a robot environment, which is very difficult to solve using the above-described conventional technologies.

Further, the present invention may provide a new method that can continuously improve the performance of human behavior recognition.

As described above, in the human behavior recognition apparatus and method according to the present invention, the configurations and schemes in the above-described embodiments are not limitedly applied, and some or all of the above embodiments can be selectively combined and configured such that various modifications are possible.

What is claimed is:

1. A human behavior recognition apparatus, comprising:
    a multimodal sensor unit for generating at least one information of image information, sound information, location information, and Internet-of-Things (IoT) information relating to a person using a multimodal sensor;
    a contextual information extraction unit for extracting contextual information for recognizing actions of the person from the at least one information;
    a human behavior recognition unit for generating behavior recognition information by recognizing the actions of the person using the contextual information and recognizing a final action of the person using the behavior recognition information and behavior intention information; and
    a behavior intention inference unit for generating the behavior intention information based on context of action occurrence related to each of the actions of the person included in the behavior recognition information,
    wherein the behavior intention inference unit checks actions previous and subsequent to a current action of the person using the behavior recognition information in order to define the context of action occurrence, and
    wherein the behavior intention information includes possible actions that are capable of occurring subsequent to the actions of the person for whom the context of action occurrence is defined,
    wherein the human behavior recognition unit determines any one of subsequent actions that are predicted from the context of action occurrence included in the behavior intention information, among actions of the person, and then recognizes the final action of the person based on the determined action.

2. The human behavior recognition apparatus of claim 1, further comprising a behavior pattern modeling unit for generating a behavior pattern model by modeling a behavior pattern of the person using the contextual information, the behavior recognition information, and the behavior intention information.

3. The human behavior recognition apparatus of claim 2, wherein the behavior pattern model includes information about a probability of occurrence of each action using times at which the actions of the person are recognized and a frequency with which the contextual information is used to recognize the actions of the person.

4. The human behavior recognition apparatus of claim 3, wherein the human behavior recognition unit sets weights, corresponding to the action occurrence probability information, for the contextual information for recognizing actions of the person using the behavior pattern model.

5. The human behavior recognition apparatus of claim 4, wherein the human behavior recognition unit recognizes the final action of the person, among possible actions of the person that are capable of occurring in a current time span, using the contextual information for which the weights are set and the action occurrence probability information.

6. The human behavior recognition apparatus of claim 5, wherein the behavior pattern modeling unit updates the action occurrence probability information based on times at which the actions of the person are recognized using the behavior pattern model, the contextual information corresponding to the actions of the person, and the behavior intention information.

7. A human behavior recognition method for a human behavior recognition apparatus, comprising:
generating at least one information of image information, sound information, location information, and Internet-of-Things (IoT) information relating to a person using a multimodal sensor;
extracting contextual information for recognizing actions of the person from the at least one information;
generating behavior recognition information by recognizing the actions of the person using the contextual information;
generating behavior intention information based on context of action occurrence related to each of the actions of the person included in the behavior recognition information; and
recognizing a final action of the person using the behavior recognition information and the behavior intention information
wherein generating the behavior intention information is configured to check actions previous and subsequent to a current action of the person using the behavior recognition information in order to define the context of action occurrence, and
wherein generating the behavior intention information is configured to generate the behavior intention information including possible actions that are capable of occurring subsequent to the actions of the person for whom the context of action occurrence is defined,
wherein recognizing the final action of the person is configured to determine any one of subsequent actions that are predicted from the context of action occurrence included in the behavior intention information, among actions of the person, and then recognize the final action of the person based on the determined action.

8. The human behavior recognition method of claim 7, further comprising generating a behavior pattern model by modeling a behavior pattern of the person using the contextual information, the behavior recognition information, and the behavior intention information.

9. The human behavior recognition method of claim 8, wherein the behavior pattern model includes information about a probability of occurrence of each action using times at which the actions of the person are recognized and a frequency with which the contextual information is used to recognize the actions of the person.

10. The human behavior recognition method of claim 9, wherein recognizing the final action of the person is configured to set weights, corresponding to the action occurrence probability information, for the contextual information for recognizing actions of the person using the behavior pattern model.

11. The human behavior recognition method of claim 10, wherein recognizing the final action of the person is configured to recognize the final action of the person, among possible actions of the person that are capable of occurring in a current time span, using the contextual information for which the weights are set and the action occurrence probability information.

12. The human behavior recognition method of claim 11, wherein generating the behavior pattern model is configured to update the action occurrence probability information based on times at which the actions of the person are recognized using the behavior pattern model, the contextual information corresponding to the actions of the person, and the behavior intention information.

* * * * *